United States Patent [19]
Nierlich et al.

[11] Patent Number: 5,998,685
[45] Date of Patent: Dec. 7, 1999

[54] PROCESS FOR PREPARING BUTENE OLIGOMERS FROM FIELD BUTANES

[75] Inventors: Franz Nierlich, Marl; Paul Olbrich, Haltern; Wilhelm Droste, Marl; Richard Mueller, Marl; Walter Toetsch, Marl, all of Germany

[73] Assignee: Huels Aktiengesellschaft, Marl, Germany

[21] Appl. No.: 08/899,897

[22] Filed: Jul. 24, 1997

[30] Foreign Application Priority Data

Jul. 24, 1996 [DE] Germany .......................... 196 29 903

[51] Int. Cl.$^6$ .............................. C07C 1/00; C07C 5/00; C07C 5/373; C07C 27/20
[52] U.S. Cl. ...................... 585/329; 585/250; 585/252; 585/253; 585/255; 568/909
[58] Field of Search ................... 585/329, 250, 585/252, 253, 255; 568/909

[56] References Cited

U.S. PATENT DOCUMENTS

| 4,392,984 | 7/1983 | Engelbach et al. ...................... 252/432 |
| 5,177,282 | 1/1993 | Nierlich et al. .......................... 585/329 |
| 5,811,608 | 9/1998 | Stine et al. .............................. 585/316 |

FOREIGN PATENT DOCUMENTS 0 149 698  7/1985  European Pat. Off. .

OTHER PUBLICATIONS

S. T. Bakas, et al., AIChE Summer Meeting, pp. 1–32, Aug. 19–22, 1990, "Production of Ethers from Field Butanes and Refinery Streams" (with English Abstract) abstract only.

Y. Chauvin, et al., Jahrgang. Heft, vol. 7/8, pp. 309–315, Jul./Aug. 1990, "Upgrading of $C_2$, $C_3$, and $C_4$ Olefins by IFP Dimersol Technology".

R. L. Espinoza, et al., Applied Catalysis, vol. 31, pp. 259–266, 1987, "Catalytic Oligomerization of Ethene Over Nickel–Exchanged Amorphous Silica–Alumina; Effect of the Nickel Concentration".

H. W. Grote, The Oil and Gas Journal, pp. 73–76, Mar. 31, 1958, "Introducing: Alkar and Butamer".

F. Nierlich, Huels Publication, Clean Fuel Technology, Hydrocarbon Processing, 2 pages, Feb. 1992, "Oligomerize for Better Gasoline".

F. Nierlich, Huels Publication, Oil Gas Refining, 6 pages, Oct. 15–16, 1992, "Recent Developments in Olefin Processing for Cleaner Gasoline".

F. Nierlich, Erdol & Kohle, Erdgas Petrochemie, AIChE 1987 Summer National Meeting, 4 pages, Aug. 16–19, 1987, "Intgrated Tert. Butyl Alcohol/Di–n–Butenes Production from FCC $C_4$'s".

R.A. Pogliano, et al., Petrochemical Review, pp. 1–22, Mar. 19–21, 1996, "Dehydrogenation–Based Ether Production Adding Value to LPG and Gas Condensate".

Bernhard Scholz, et al., Methyl Tert–Butyl Ether, vol. A 16, pp. 543–550, "Methyl Tert–Butyl Ether".

G. C. Sturtevant, et al., UOP Technology Conference, pp. 2,4,6,8,10,12,14,16 and 18, 1988, "Oleflex Selective Production of Lights Olefins".

K. H. Walter, et al., DGMK–Conference, 34 pages, Nov. 11–12, 1993, "Selective Hydrogenation and Dehydrogenation".

*Primary Examiner*—Paul J. Killos
*Assistant Examiner*—J. Parsa
*Attorney, Agent, or Firm*—Oblon, Spivak, McClelland, Maier & Neustadt, P.C.

[57] ABSTRACT

A highly flexible process for preparing butene oligomers from field butanes. The process can be controlled to produce the desired oligomerization products by appropriate selection of the starting materials.

16 Claims, 1 Drawing Sheet

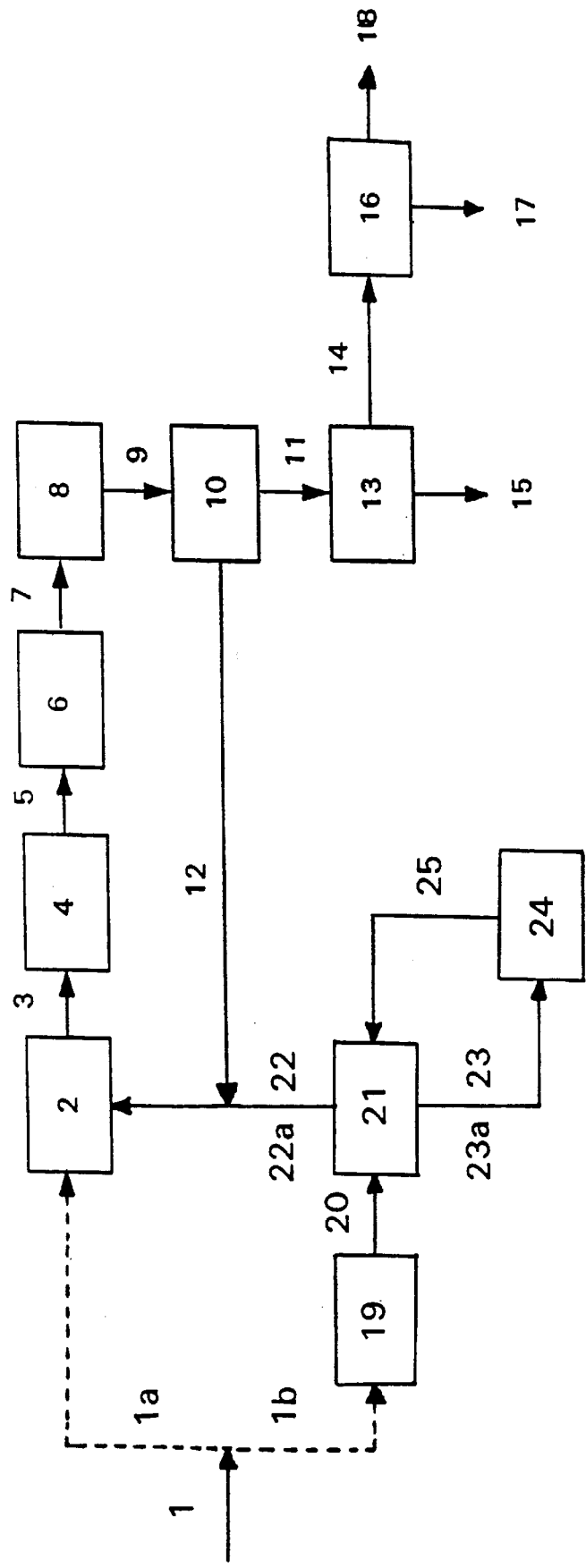
Figure

PROCESS FOR PREPARING BUTENE OLIGOMERS FROM FIELD BUTANES

BACKGROUND OF THE INVENTION

1. Field of the Invention

The present invention relates to a process for preparing butene oligomers, which are valuable starting materials for plasticizer alcohols, from field butanes. The process is highly flexible because the oligomer products may be determined by judicious selection of the starting materials.

2. Description of the Background

Dibutenes are an isomeric mixture which are formed, in addition to higher butene oligomers, by dimerization and/or codimerization of butenes, i.e., of n-butene and/or isobutene, in the oligomerization of butenes. The term di-n-butene refers to the dimerization product of n-butene, i.e., dimerization 1-butene and/or 2-butene. Important components of di-n-butene are 3-methyl-2-heptene, 3,4-dimethyl-2-hexene and, to a lesser extent n-octenes. The term dibutene may also refer to the dimerization products obtained by the reaction of n-butene and isobutene. Di-isobutene is the mixture of dimers which is formed by dimerization of isobutene. Di-isobutene contains molecules which are more highly branched than dibutene, and this, in turn, is more highly branched than di-n-butene.

Dibutene, di-n-butene and di-isobutene are starting materials for preparing isomeric nonanols by hydroformylation and hydrogenation of the $C_9$ aldehydes thus formed. Esters of these nonanols, in particular the phthalic esters, are plasticizers which are prepared to a significant extent, and are primarily used for poly(vinyl chloride). Nonanols from di-n-butene are linear to a greater extent than nonanols from dibutene, which are in turn less branched than nonanols from di-isobutene. Esters of nonanols from di-n-butene, because of their more linear structure, have application advantages as compared to esters of nonanols obtained from dibutene or di-isobutene, and are particularly in demand.

Butenes can be obtained for the dimerization reaction to form dibutenes from the $C_4$ fraction of steam crackers or of FC crackers, for example. This $C_4$ fraction is generally worked up by first separating off 1,3-butadiene by a selective scrubbing, e.g., using n-methylpyrrolidone. Isobutene is a desirable and particularly valuable $C_4$ fraction component because it may be chemically reacted to give sought-after products, e.g., with isobutane to provide high-octane iso-octane or with methanol to afford methyl tert-butyl ether (MTBE), which, as an additive to motor gasoline, improves its octane rating. After the reaction of the isobutene, the n-butenes, n-butane and isobutane remain behind. The proportion of n-butenes in the cracking products of the steam cracker or the FC cracker is relatively low, however, approximately 10 percent by weight, based on the principal target product ethylene. A steam cracker having the respectable capacity of 600,000 metric t/year of ethylene therefore only provides about 60,000 metric t/year of n-butene. Although this amount (and that of the isobutenes) could be increased by dehydrogenating the approximately 15,000 metric t/year of n-butane and isobutane which arise in addition to the n-butenes, this is not advisable, because dehydrogenation plants require high capital expenditure and are not economic for such a small capacity.

Isobutene is, as discussed above, a cracking product in high demand, and is therefore not generally available for the oligomerization reaction to produce n-butenes. The amount of n-butenes which a steam cracker or an FC cracker produces directly is not sufficient, however, to produce sufficient dibutene for a nonanol plant whose capacity is high enough that it could compete economically with the existing large-scale plants for preparing important plasticizer alcohols, such as 2-ethylhexanol. Butenes from several different steam crackers or FC crackers would therefore have to be collected and oligomerized together, in order to meet the dibutene demand of a large nonanol plant. Opposing this, however, is the fact that the transport of liquefied gases is expensive, not least because of the complex safety precautions required to do so.

It would be desirable if butenes could be provided at only one site without transport over relatively large distances in amounts for the oligomerization as are required for the operation of a large scale plant for preparing nonanols having a capacity of 200,000 to 800,000 metric t/year, for example. It would also be desirable to have a process for preparing butene oligomers in which the valuable di-n-butene product can be separated off from the dibutene product mixture. Finally, it would be desirable if the process could be controlled in such a manner that, in addition to higher butene oligomers, only di-n-butene or di-isobutene is formed as the dibutene product.

SUMMARY OF THE INVENTION

It is an object of the present invention to provide a highly flexible process for producing butene oligomers from field butanes. The final product obtained in the process may be controlled by selection of the starting materials used in the oligomerization reaction.

This object and other may be accomplished with a process for preparing butene oligomers from field butanes by:

(a) dehydrogenating the n-butane, isobutane or both, present in a field butane in a dehydrogenation stage; and (b) oligomerizing the dehydrogenation mixture in an oligomerization stage to provide an oligomerization reaction mixture.

This embodiment of the present process is referred to as Variant A below.

In a preferred embodiment, referred to as Variant B below, the oligomerization reaction produces dibutene which is separated off from the other oligomers after first removing the residual gases contained in the oligomerization mixture.

In another preferred embodiment, referred to as Variant C below, the oligomerization reaction produces dibutene, and the di-n-butene is separated from the dibutene mixture.

In another particularly preferred embodiment, referred to as Variant D below, the process is controlled in such a manner that, in addition to higher butene oligomers, only di-n-butene is formed, by separating off n-butane by fractional distillation from, optionally, a previously hydrogenated, field butane, isomerizing the remaining isobutane in an isomerization stage to provide a mixture of n-butane and isobutane, separating off the n-butane from the isomerization mixture by fractional distillation and conducting it into the dehydrogenation stage together with the n-butane separated off directly from the field butane, and recycling the remaining isobutane into the isomerization stage.

In still another preferred embodiment, referred to as Variant E below, the process may be controlled in such a manner that, in addition to higher butene oligomers, only di-isobutene is formed, by separating isobutane by fractional distillation from the, optionally, previously hydrogenated, field butane, isomerizing the remaining n-butane in an isomerization stage to provide a mixture of n-butane and isobutane, separating off the isobutane from the isomerization mixture by fractional distillation and conducting it into the dehydrogenation stage, together with the isobutane separated off directly from the field butane and recycling the remaining n-butane into the isomerization stage.

A more complete appreciation of the invention and many of the attendant advantages thereof will be readily obtained as the same becomes better understood by reference to the following detailed description when considered in connection with the accompanying drawing.

BRIEF DESCRIPTION OF THE DRAWING

The FIGURE shows a block diagram of the present according to the present invention. The field butane 1 is used as stream 1a in the Variants A, B and C of the present process; the alternative stream 1b is used in Variants D and E.

DETAILED DESCRIPTION OF THE INVENTION

The process according to the invention with its Variants A to E is distinguished by high flexibility. Therefore, depending on market requirements, if desired, only di-n-butene, dibutene, and other dibutenes conjointly or only di-isobutene can be produced, even if the latter will only rarely be the desired main product.

The term "field butanes" refers to the $C_4$ fraction of the "moist" portions of the natural gas and of the crude oil-associated gases which are separated off from the gases in liquid form by cooling to about −30° C. Low-temperature distillation produces therefrom the field butanes, whose composition fluctuates with the field, but which generally contain about 30% isobutane and 65% n-butane. Further components are generally about 2% $C_{<4}$ hydrocarbons and about 3% $C_{>4}$ hydrocarbons. Field butanes may be used without separation as feedstuffs in steam crackers or as an additive to motor gasoline. They may be resolved into n-butane and isobutane by fractional distillation. Isobutane is used, for example, to a considerable extent for preparing propylene oxide by cooxidation of propylene and isobutane and is also used as alkylating agent, by which n-butene or isobutene is alkylated to give isooctane, which is valued as an additive to motor gasoline because of its high octane rating. n-Butane, in contrast, has found fewer such important uses. It serves, for example, as butane gas for heating purposes or is used in relatively small amounts, e.g., for preparing polymers or copolymers or maleic anhydride by atmospheric oxidation. Formerly, n-butane was also dehydrogenated via the n-butene stage to give 1,3-butadiene, but this process has become uneconomic in the interim. Because isobutane is the more sought-after component of the field butane, n-butane may be isomerized on a large scale to isobutane (cf., e.g. R. A. Pogliano et. al., Dehydrogenation-based Ether Production, 1996 Petrochemical Review. DeWitt & Company, Houston, Tex., Butamer® process, page 6-1 and S. T. Bakas, F. Nierlich et al., Production of Ethers from Field Butanes and Refinery Streams, AlChE Summer Meeting, 1990, San Diego, Calif.2, page 11). It was not therefore part of the technological trend in the art to develop a process which, as in the Variants A, B and C, uses the n-butane in the field gas, from which preferred nonanols are prepared via the intermediate di-n-butene. The present invention runs counter to the technological trend particularly when the usually sought-after isobutane is isomerized to n-butane, as in Variant D.

Variant A

The field butanes 1a are first dehydrogenated in the dehydrogenation stage 2. The dehydrogenation is a codehydrogenation. It is remarkable that the dehydrogenation of the field butane which is a mixture of components having different dehydrogenation behaviors succeeds so readily. The process condition substantially correspond to those as are known for n-butane and isobutane or other lower hydrocarbons. Thus, S. T. Bakas, F. Nierlich et al., loc. cit., pages 12 ff., incorporated herein by reference, describe the Oleflex® process which is generally suitable for the selective preparation of light olefins and by which isobutane can be dehydrogenated to isobutene with a selectivity of 91 to 93%. Further relevant publications are those of G. C. Sturtevant et al., Oleflex— Selective Production of Light Olefins, 1988 UOP Technology Conference and EP 0 149 698, both incorporated herein by reference.

The dehydrogenation is expediently carried out in the gas phase on fixed-bed or fluidized catalysts, e.g. on chromium (111) oxide or, advantageously, on platinum catalysts having aluminum oxide or zeolites as a support. The dehydrogenation generally takes place at temperatures of 400 to 800° C., preferably from 550 to 650° C. Atmospheric pressure or slightly elevated pressure of up to 3 bar is generally employed. The residence time in the catalyst bed is generally between 1 and 60 minutes, depending on catalyst, temperature and desired degree of conversion. The throughput is preferably between 0.6 to 36 kg of field butane per $m^3$ of catalyst and hour.

It is preferable to carry out the dehydrogenation only until about 50% of the n-butane and isobutane remain unchanged in the dehydrogenation mixture 3. Although higher degrees of conversion may be attained at higher temperature, cracking reactions which decrease the yield proceed to an increasing extent, owing to coke deposits, which reduce the service life of the dehydrogenation catalyst. The optimum combinations of the reaction conditions which lead to the desired degrees of conversion, such as type of catalyst, temperature and residence time, may be determined without difficulty.

The dehydrogenation mixture 3 generally contains 90 to 95% $C_4$ hydrocarbons and, in addition, hydrogen and lower- and higher-boiling portions which, in part, originate from the field butane 1, and, in part, are formed in the dehydrogenation stage 2. Purification is preferably performed upstream of the oligomerization. In a first purification stage, the $C_4$ fraction and the higher-boiling portions may be condensed out. The condensate is distilled under pressure, cocondensed dissolved $C_{<4}$ hydrocarbons passing overhead. From the bottom product, in a further distillation the $C_4$ hydrocarbons are obtained as main product and the comparatively small amount of $C_{>4}$ hydrocarbons is obtained as a residue.

The $C_4$ hydrocarbons, depending on the degree of conversion, may contain small amounts, such as 0.01 to 5% by volume, of dienes such as 1,3-butadiene. It is advisable to remove this component since, even in markedly lower amounts, it can damage the oligomerization catalyst. A suitable process is selective hydrogenation 4 which, in addition, increases the proportion of the desired n-butene. A suitable process has been described, e.g., by F. Nierlich et. al. in Erdöl & Kohle, Erdgas, Petrochemle, 1986, pages 73 ff, incorporated herein by reference. It operates in the liquid phase with completely dissolved hydrogen in stoichiometric amounts. Selective hydrogenation catalysts which are suitable are, e.g., nickel and, in particular, palladium, on a support, e.g., 0.3 percent by weight of palladium on activated carbon or, preferably, on aluminum oxide. A small amount of carbon monoxide in the ppm range promotes the selectivity of the hydrogenation of 1,3-butadiene to give the monoolefins and counteracts the formation of polymers, the so-called "green oil", which can inactivate the catalyst. The process generally operates at room temperature or elevated temperatures up to about 60° C. and at elevated pressures which are preferably in the range of up to 20 bar. The content of 1,3-butadiene in the $C_4$ fraction of the dehydrogenation mixture may be decreased in this manner to values of <1 ppm.

It is also preferable to pass the dehydrogenation mixture 5 $C_4$ fraction, which is then substantially free (e.g., less than 1 ppm) from 1,3-butadiene, via the purification stage 6, a molecular sieve, upstream of the oligomerization stage, as a result of which further substances which are harmful for the oligomerization catalyst are removed and its service life is further increased. These harmful substances include oxygen compounds and sulfur compounds. This process has been described by F. Nierlich et al. in EP-B 0 395 857, incorporated herein by reference. A molecular sieve having a pore diameter of 4 to 15 angstroms, advantageously 7 to 13 angstroms, is preferably used. In some cases it is expedient for economic reasons to pass the dehydrogenation mixture successively over molecular sieves having different pore sizes. The process may be carried out in the gas phase, in liquid phase or in gas-liquid phase. The pressure is preferably 1 to 200 bar. Room temperature or elevated temperatures up to 200° C. are expediently employed.

The chemical nature of the molecular sieves is less important than their physical properties, i.e., in particular, the pore size. The most diverse molecular sieves can therefore be used, both crystalline natural aluminum silicates, e.g., sheet lattice silicates, and synthetic molecular sieves, e.g., those having a zeolite structure. Zeolites of the A, X and Y type are available, inter alia, from Bayer AG, Dow Chemical Co., Union Carbide Corporation, Laporte Industries Ltd., and Mobil Oil Co. Suitable synthetic molecular sieves for the process are also those which, in addition to aluminum and silicon, also contain other atoms introduced by cation exchange, such as gallium, indium or lanthanum, as well as nickel, cobalt, copper, zinc or silver. In addition, synthetic zeolites are suitable in which, in addition to aluminum and silicon, still other atoms, such as boron or phosphorus, have been incorporated into the lattice by mixed precipitation.

As discussed above, the selective hydrogenation stage 4 and the purification stage 6 using a molecular sieve are optional, advantageous measures for the process according to the invention. Their order is, in principle, optional, but the order specified in the FIGURE is preferred.

The dehydrogenation mixture 7, if appropriate, pretreated as described above, is passed into the oligomerization stage 8, which is an essential part of the present process. The oligomerization is a cooligomerization of n-butenes and isobutene which is carried out in a manner known per se, such as has been described, e.g., by F. Nierlich in Oligomerization for Better Gasoline, Hydrocarbon Processing, 1992, pages 45 ff, or by F. Nierlich et al. in the previously mentioned EP-BL 0 395 857. Both of these publications are incorporated herein by reference. The procedure is generally carried out in the liquid phase and, as homogeneous catalyst, a system is employed, e.g., which comprises nickel (11) octoate, ethylaluminum chloride and a free fatty acid (DE-C 28 55 423, incorporated herein by reference), or preferably one of the numerous known fixed-bed catalysts or catalysts suspended in the oligomerization mixture which are based on nickel and iron. The catalysts frequently additionally contain aluminum. Thus, DD-PS 160 037, incorporated herein by reference, describes the preparation of a nickel- and aluminum-containing precipitated catalyst on silicon dioxide as support material. Other useful catalysts are obtained by exchanging positively charged particles, such as protons or sodium ions, which are situated on the surface of the support materials, for nickel ions. This is successful with the most diverse support materials, such as amorphous aluminum silicate (R. Espinoza et al., Appl. Kat., 31 (1987) pages 259–266; crystalline aluminum silicate (DE-C 20 29 624); zeolites of the ZSM type (NL Patent 8 500 459); an X zeolite (DE-C 23 47 235); X and Y zeolites (A. Barth et al., Z. Anorg. Allg. Chem. 521, (1985) pages 207–214); and a mordenite (EP-A 0 233 302). All of these publications are incorporated herein by reference.

The cooligomerization is expediently carried out, depending on the catalyst, at 20 to 200° C. and under pressures of 1 to 100 bar. The reaction time (or contact time) is generally 5 to 60 minutes. The process parameters, in particular the catalyst type, the temperature and the contact time, are matched to one another in such a manner that the desired degree of oligomerization is attained. In the case of nonanols as the desired target product, this is predominantly a dimerization, i.e., dibutenes are the main product. For this purpose, clearly the reaction should not proceed to full conversion, but conversion rates of 30 to 70% per pass are preferred. The optimum combinations of the process parameters are easily determined.

The residual gas 12 may be separated off from the oligomerization mixture 9 in a separation stage 10 and recycled to the dehydrogenation stage 2. If a catalyst of the liquid catalyst type discussed above was used in the oligomerization stage 8, the residual gas 12 is preferably purified in advance to protect the dehydrogenation catalyst. The oligomerization mixture may be initially treated with water, in order to extract the catalyst components. The residual gas 12 separated off may then be dried with a suitable molecular sieve, where other minor components are also separated off. Then polyunsaturated compounds, such as butynes, may be removed by selective hydrogenation, e.g., on palladium catalysts, and the residual gas 12 thus purified may be recycled into the dehydrogenation stage 2. These measures for purifying the residual gas 12 are unnecessary if a solid oligomerization catalyst is used.

The oligomers 11 remaining after separating off the residual gas 12 are suitable, because of their branched components, as an additive to motor gasoline to improve the octane rating.

Variant B

The oligomers 11 are separated in the distillation stage 13 into dibutenes 14, and trimers 15, i.e., isomeric dodecenes, and other higher oligomers, where the main fraction comprises the desired dibutenes 14. The dodecenes 15 can be hydroformylated, the hydroformylation products can be hydrogenated and the tridecanols thus obtained can be ethoxylated, as a result of which valuable detergent bases are obtained. The dibutenes 14 are directly suitable as starting material for preparing nonanol. The dibutenes can also be hydroformylated and the hydroformylation product then oxidized to produce at lest one nonanoic acid.

Variant C

If the particular properties of the nonanols from di-n-butene are of interest, the dibutenes 14 are separated in the fine distillation stage 16 into di-n-butene 17 and the residual dibutenes 18 which, as more highly branched molecules are lower boiling, which residual dibutenes can likewise be used for preparing nonanols or can be added to motor gasoline.

This procedure is a more expedient alternative to the variant in which n-butene and isobutene are separated off from the codehydrogenation mixture 7 by distillation and these isomers are oligomerized separately. This variant would require two separate oligomerization stages, which would be considerably more capital-intensive and also more complex in operation than only one, albeit larger, cooligomerization stage 8 in combination with a fine distillation stage 16.

Variant D

This variant of the present process is used when it is desired to prepare only di-n-butene as the dibutene product. If the field butane 1b contains olefinically unsaturated components, it is advantageously first passed into a hydrogenation stage 19, because these components can interfere with the later isomerization of the isobutane. The hydrogenation proceeds in a manner known per se, such as described by K. H. Walter et al., in the Hüls Process for Selective Hydrogenation of Butadiene in Crude $C_4$'s, Development and Technical Application, DGKM meeting Kassel, November 1993, incorporated herein by reference. The procedure is therefore expediently carried out in the liquid phase and, depending on the catalyst, at room temperature or elevated temperature up to 90° C. and at a pressure of 4 to 20 bar, the partial pressure of the hydrogen being 1 to 15 bar. The catalysts customary for the hydrogenation of olefins are used, e.g. 0.3% palladium on aluminum oxide.

The hydrogenated field butanes 20 are passed into the separation stage 21. This generally comprises a highly effective column in which n-butane 22 and isobutane 23 are separated by fractional distillation. The column 21 is operated in a customary manner, expediently at a pressure of from 4 to 7 bar. The $C_{>4}$ hydrocarbons arise as bottom product, n-butane 22 is taken off in the side stream and passes, together with the residual gas 12, into the dehydrogenation 2 and the isobutane 23 which boils around 10 to 20° C. lower, together with lighter ends, passes into the isomerization stage 24, in which the isobutane is converted into n-butane at most up to an equilibrium which, depending on temperature, is approximately 40 to 55% n-butane and 45 to 60% isobutane. The isomerization of n-butane and isobutane is a known reaction, albeit generally with the aim of obtaining isobutane (see, e.g., H. W. Grote, Oil and Gas Journal, 56 (13 pages 73 ff., (1958), incorporated herein by reference). The procedure is generally carried out in the gas phase, expediently at a temperature of 150 to 230° C. at a pressure of 14 to 30 bar and using a platinum catalyst on aluminum oxide as support, whose selectivity can be further improved by doping with a chlorine compound, such as carbon tetrachloride. Advantageously, a small amount of hydrogen is added, in order to counteract a dehydrogenation. The selectivity of the isomerization to n-butane is high, cracking to form smaller fragments only takes place to a minor extent (approximately 2%).

The isomerization mixture 25 is preferably separated into the isomers. This is expediently performed in the column 21 which is present in any case, from which n-butane passes into the dehydrogenation stage 2 which, in contrast to Variants A, B and C, is not a codehydrogenation stage. In its further process steps, Variant D corresponds to the other variants of the process. In the oligomerization stage 8, a cooligomerization again proceeds, since the n-butene from the dehydrogenation stage 2 is actually a mixture of 1-butene and 2-butene. The fine distillation stage 16 may be omitted, however, since the dibutene 14 is already di-n-butene.

Variant E

This variant is selected when only di-isobutene is desired as the dibutene product. Isobutane is used as the starting material in the oligomerization for this embodiment of the invention. The arrangement of Variant D is used, except that isobutane 22a is passed from the column 21 into the dehydrogenation stage 2, in which again, as in Variant D and unlike in Variants A, B and C, no codehydrogenation takes place. The n-butane 23a is passed from the column 21 into the isomerization stage 24 and there isomerized to isobutane at most up to equilibrium. The isobutane is separated from n-butane, again expediently in the column 21, and likewise passed into the dehydrogenation stage 2, whereas the n-butane returns to the isomerization stage 24. In this manner, the n-butane may be completely converted into isobutane. The dehydrogenation mixture 3 is expediently purified as described in Variant A. The oligomerization in the oligomerization stage 8 is a homo-oligomerization, because only isobutane participates therein, and di-isobutene arises in the distillation stage 13. The fine distillation 16 is likewise omitted.

This application is based on German patent application serial No. 196 29 903.9, filed Jul. 24, 1996 and incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

Example for O.Z. 5073-US

Dehydrogenation

The first step of the process according to the invention consists of the dehydrogenation of the field butanes. For this purpose, a dehydrogenation system on a laboratory scale was used. It consisted of a reactor, hydrogen separation zone and heaters, pumps, compressors, and the other usual devices for handling liquid gases.

The dehydrogenation catalyst and its production are described in detail in EP-OS 0 149 698. The catalyst used here consisted of 0.71 weight-% Pt, 0.4 weight-% Sn, 2.9 weight-% K and 3.1 weight-% Cl on a gamma aluminum oxide carrier.

The inflowing stream with the hydrocarbons to be dehydrogenated was mixed with hydrogen in such a way that a molar ratio of hydrogen to hydrocarbons of 1.5:1 was adjusted. The reaction temperature was 645° C., the pressure was 0.2 MPa.

The hydrocarbons were passed through the reactor at an LHSV of 5/h, in a straight pass.

The dehydrogenation product was cooled with acetone/dry ice at the reactor exit, and collected in a storage vessel. The analyses yielded the following results:

TABLE 1

| Composition of the hydrocarbons in wt.-% | | |
| --- | --- | --- |
| Component | Reactor intake | Product |
| n-butane | 65.13 | 38.38 |
| isobutane | 29.92 | 16.45 |
| n-butene | 0.01 | 21.71 |
| isobutene | 0.02 | 11.84 |
| substances with a high boiling point (C5+) | 2.20 | 4.41 |
| substances with a low boiling point (C3-) | 2.81 | 7.22 |
| 1,3-butadiene | 0.01 | 1.11 |

Separation of Substances with a Low Boiling Point

To separate the hydrocarbons with a chain length of three or fewer carbon atoms, the product of the dehydrogenation system was moved from the storage vessel to the 40th level of a distillation column with 80 practical levels, at 5000 g/h.

The distillation column was operated at a head pressure of 0.82 MPa with a head temperature of 55° C. and a sump temperature of 66° C., with a reflux of 3500 g/h. The dehydrogenation product, from which the substances with a low boiling point had been removed, was continuously drawn off from the sump, regulated according to the level, at approximately 4650 g/h, cooled with acetone/dry ice, and collected, and had the composition indicated in Table 2.

TABLE 2

Composition of the dehydrogenation product after removal of substances with a low boiling point

| Component | Product (wt.-%) |
|---|---|
| n-butane | 40.86 |
| isobutane | 17.52 |
| n-butene | 23.12 |
| isobutene | 12.61 |
| substances with a high boiling point (C5+) | 4.70 |
| substances with a low boiling point (C3-) | 0.01 |
| 1,3-butadiene | 1.18 |

Separation of Substances with a High Boiling Point

To separate the hydrocarbons with a chain length of five or more carbon atoms, the product of the dehydrogenation system, from which the substances with a low boiling point had been removed, was moved from the storage vessel into a distillation column with 50 practical levels, at 1000 g/h.

The distillation column was operated at a pressure of 0.6 MPa and a head temperature of 50° C. The distillate was continuously drawn off from the distillate presentation at approximately 950 g/h, cooled with acetone/dry ice, and collected. It had the composition indicated in Table 3.

TABLE 3

Composition of the dehydrogenation product after removal of substances with a low boiling point and substances with a high boiling point

| Component | Product (wt.-%) |
|---|---|
| n-butane | 42.70 |
| isobutane | 18.41 |
| n-butene | 24.24 |
| isobutene | 13.31 |
| substances with a high boiling point (C5+) | 0.01 |
| substances with a low boiling point (C3-) | 0.01 |
| 1,3-butadiene | 1.32 |

Selective Hydrogenation

Selective hydrogenation of the butadiene to produce n-butenes was carried out in a fixed-bed laboratory reactor with an external circuit. Recycling was selected in such a way that a butadiene concentration of 0.8% prevailed in the intake flow to the reactor. Hydrogen was metered into the intake of the reactor at a molar ratio of $H_2$/1,3-butadiene= 1.2/1. In addition, a concentration of 2 ppm carbon monoxide was adjusted in the intake. 0.5% Pd on aluminum oxide served as the catalyst. The reactor was operated at 2 MPa and 30° C. with an LHSV of 20/h.

At the reactor exit, product was continuously removed from the circuit: its composition is shown in Table 4.

TABLE 4

Composition of the product of selective hydrogenation

| Component | Product (wt.-%) |
|---|---|
| n-butane | 42.71 |
| isobutane | 18.41 |
| n-butene | 25.55 |
| isobutene | 13.31 |
| substances with a high boiling point (C5+) | 0.01 |
| substances with a low boiling point (C3-) | 0.01 |
| 1,3-butadiene | <1 ppm |

Oligomerization with Pre-purification

In the next step of the process according to the invention, the product of selective hydrogenation was first passed from a supply vessel over an adsorption bed comprised of a molecular screen with a pore diameter of 3 Angstroms and at an LHSV of 5/h. Then, the solution pre-treated in this way was passed over a molecular screen, Type 13 X from Bayer AG (pore diameter 9 Angstroms) at an LHSV of 4/h.

The solution pre-treated in this way was now oligomerized at a temperature of 70° C. a pressure of 2.5 MPa, and an LHSV of 4/h, in accordance with EP patent 0 395 857 B1, on a nickel-exchanged montmorillonite (montmorillonite from Fluka AG, described by: J. R. Sohn, H. B. Park. J. Kor. Chem. Soc. 26(5), p. 282 ff, 1982). The total conversion to olefins was 29% in this stage.

TABLE 5

Composition of the oligomerization product

| Component | Product (wt.-%) |
|---|---|
| n-butane | 42.71 |
| isobutane | 18.41 |
| n-butene | 22.55 |
| isobutene | 5.04 |
| dibutene | 9.02 |
| tributene/tetrabutene | 2.25 |

The dibutenes had the following composition.

TABLE 6

Composition of the dibutene

| Component | Product (wt.-%) |
|---|---|
| 2,2,4-trimethyl pentene | 16.77 |
| 2,3,4-trimethyl pentene | 12.89 |
| 2,3,3-trimethyl pentene | 5.30 |
| 2,2,3-trimethyl pentene | 20.43 |
| 2,5-dimethyl hexene | 10.22 |
| 2,2-dimethyl hexene | 1.47 |
| 3,4-dimethyl hexene | 7.61 |
| 3-methyl heptene | 19.48 |
| n-octene | 4.72 |

Separation of Residual Gas

The butenes were separated from the oligomerization product. For this purpose. a column with 15 levels was used. which was operated at 0.35 Mpa. 52° C. head temperature, and 192° C. sump temperature. The column was operated with a continuous intake of 2000 kg/h. An average of 1770 kg/h was removed from the distillate container, and this could be used as the raw material for renewed dehydrogenation. The oligomer mixture was drawn off from the sump, at approximately 230 g/h, regulated on the basis of level, and it was stored in a storage container at normal conditions. The oligomer mixture from which the residual gas had been removed had the following composition.

TABLE 7

Composition of the oligomer mixture from which residual gas has been removed

| Component | Product (wt.-%) |
| --- | --- |
| dibutenes | 79.92 |
| tributenes/tetrabutenes | 20.06 |

Separation of the Higher Oligomers

Separation of the dibutenes from the tributene/tetrabutenes and of other higher oligomers took place in a glass column packed with Raschig rings, which was operated at a pressure of 40 kPa abs, a head temperature of 84° C. and a sump temperature of 167° C.

The intake was 700 g.h. Approximately 540 g/h were continuously drawn off from the distillate container and collected in an intermediate container.

TABLE 8

Composition of the purified dibutene

| Component | Product (wt.-%) |
| --- | --- |
| 2,2,4-trimethyl pentene | 16.93 |
| 2,3,4-trimethyl pentene | 13.05 |
| 2,3,3-trimethyl pentene | 5.43 |
| 2,2,3-trimethyl pentene | 20.56 |
| 2,5-dimethyl hexene | 10.28 |
| 2,2-dimethyl hexene | 1.60 |
| 3,4-dimethyl hexene | 7.66 |
| 3-methyl heptene | 19.63 |
| n-octene | 4.85 |

Microdistillation

The dibutene obtained from the previous step was distilled by discontinuous fractionation in a column with 300 theoretical separation steps. A 6 m glass column NW 50 with a Sulzer EX packing was used. The work was carried out at normal pressure, and the temperatures were 109 to 127° C. in the sump, depending on the fraction, and 101 to 123° C. in the head, depending on the fraction. The dibutene was separated into 20 fractions, each of which was analyzed separately. First, the trimethyl pentenes pass over the head, followed by the dimethyl hexenes and methyl heptenes. The n-octenes, with a higher boiling point, cannot be completely separated from (cis and trans) 3-methyl heptene-2. In addition, small amounts of 3,4-dimethyl hexene-3 are still found in the fractions separated last, which contain highly concentrated di-n-butene and therefore represent the desired product. The concentrations of the isomers for fractions 2 and 19, compiled as groups, are listed in the following table as examples.

TABLE 9

Composition of two fractions of microdistillation

| Component | Amount of dibutene (wt.-%) | Fraction 2 (wt.-%) | Fraction 19 (wt.-%) |
| --- | --- | --- | --- |
| trimethyl pentenes | 45.69 | 83.71 | — |
| dimethyl hexenes | 29.82 | 9.52 | 1.11 |
| methyl heptenes | 19.63 | 6.77 | 50.95 |
| n-octenes | 4.85 | — | 47.58 |

What is claimed as new and desired to be secured by Letters Patent of the United States is:

1. A process for preparing butene oligomers from field butanes, comprising:
    dehydrogenating a field butane comprising n-butane, isobutane, or both, to produce a mixture comprising n-butene, isobutene, or both;
    oligomerizing the mixture to produce a mixture comprising dibutenes, higher butene oligomers and residual gas,
    removing the residual gas from the product mixture; and
    separating the dibutenes from the product mixture.

2. The process according to claim 1, further comprising prior to the dehydrogenating stage, removing the isobutane from a field butane comprising isobutane and n-butane to produce a field butane comprising the n-butane.

3. The process of claim 2, wherein the removing step comprises separating the n-butane from the isobutane by a first fractional distillation.

4. The process of claim 3, wherein the removing step further comprises isomerizing the isobutane isolated from the first fractional distillation to provide a mixture of n-butane and isobutane;
    separating the -n-butane from the isobutane contained in the isomerization reaction mixture by a second fractional distillation;
    combining the n-butane isolated from the second fractional distillations with the field butane comprising n-butane isolated from the first fractional distillation; and
    isomerizing the isobutane isolated from the second fractional distillation to produce n-butane and isobutane.

5. The process according to claim 1, further comprising prior to the dehydrogenating stage, removing the n-butane from a field butane comprising isobutane and n-butane to produce a field butane comprising the isobutane.

6. The process of claim 5, wherein the removing step comprises separating the isobutane from the n-butane by a first fractional distillation.

7. The process of claim 6, wherein the removing step further comprises isomerizing the n-butane isolated from the first fractional distillation to provide a mixture of n-butane and isobutane;
    separating the isobutane from the n-butane contained in the isomerization reaction mixture by a second fractional distillation;
    combining the isobutane isolated from the second fractional distillations with the field butane comprising isobutane isolated from the first fractional distillation; and
    isomerizing the n-butane isolated from the second fractional distillation to produce n-butane and isobutane.

8. The process according to claim 1, further comprising prior to the dehydrogenating stage, hydrogenating the field butane comprising n-butane, isobutane, or both.

9. The process according to claim 1, wherein the field butane comprising n-butene, isobutene, or both further comprises dienes and the process further comprises between the dehydrogenating step and the oligomerizing step:

selectively hydrogenating the dienes to monoolefins.

10. The process according to claim 9, further comprising between the dehydrogenating step and the oligomerizing step:

contacting the selectively hydrogenated field butane with at least one molecular sieve.

11. The process according to claim 1, further comprising between the dehydrogenating step and the oligomerizing step:

contacting the field butane comprising n-butene, isobutene, or both with at least one molecular sieve.

12. The process according to claim 1, wherein the process further comprises:

separating the residual gas from the oligomerization reaction mixture; and recycling the separated residual gas to the dehydrogenation step.

13. The process according to claim 1, further comprising isolating the di-n-butene in the dibutenes by a distillation.

14. The process according to claim 1, wherein the process further comprises:

hydroformylating the dibutenes; and hydrogenating the hydroformylation reaction product to produce at least one nonanol.

15. The process according to claim 1, wherein the process further comprises:

hydroformylating the dibutenes; and oxidizing the hydroformylation reaction product to produce at least one nonanoic acid.

16. The process according to claim 1, wherein the process further comprises:

separating dodecenes from the product mixture;

hydroformulating the dodecenes;

hydrogenating the hydroformylation reaction product; and ethoxylating the hydrogenation reaction mixture to produce a detergent base.

* * * * *